(12) United States Patent
Huang et al.

(10) Patent No.: US 9,820,443 B2
(45) Date of Patent: Nov. 21, 2017

(54) **INDUSTRIAL SCALE PROCESS OF CULTIVATING *GANODERMA LUCIDUM* MYCELIUM**

(71) Applicant: Double Crane Biotechnology Co., LTD, Taipei (TW)

(72) Inventors: Li-Ming Huang, Tainan (TW); Chih-Wei Chen, Tainan (TW); Mon-Tarng Chen, Tainan (TW); Yen-Chun Liu, Miaoli County (TW); Kuang-Dee Chen, Chiayi (TW)

(73) Assignee: DOUBLE CRANE BIOTECHNOLOGY CO. LTD., Taipei (TW)

( * ) Notice: Subject to any disclaimer, the term of this patent is extended or adjusted under 35 U.S.C. 154(b) by 292 days.

(21) Appl. No.: 14/779,498

(22) PCT Filed: Aug. 9, 2013

(86) PCT No.: PCT/CN2013/081204
§ 371 (c)(1),
(2) Date: Sep. 23, 2015

(87) PCT Pub. No.: WO2015/018076
PCT Pub. Date: Feb. 12, 2015

(65) Prior Publication Data
US 2016/0044872 A1    Feb. 18, 2016

(51) Int. Cl.
| | |
|---|---|
| *A01G 1/04* | (2006.01) |
| *C12N 1/14* | (2006.01) |
| *C12P 15/00* | (2006.01) |
| *C12M 1/12* | (2006.01) |
| *C12M 1/00* | (2006.01) |

(52) U.S. Cl.
CPC ............. *A01G 1/04* (2013.01); *C12M 23/04* (2013.01); *C12M 29/00* (2013.01); *C12M 31/00* (2013.01); *C12N 1/14* (2013.01); *C12P 15/00* (2013.01)

(58) Field of Classification Search
CPC .................................. C12N 1/14; C12N 1/20
USPC ......................................................... 47/59 R
See application file for complete search history.

(56) References Cited

U.S. PATENT DOCUMENTS

| | | | | |
|---|---|---|---|---|
| 6,316,002 | B1 * | 11/2001 | Liu | A61K 36/074 424/195.15 |
| 6,440,420 | B1 * | 8/2002 | Liu | A61K 36/074 424/195.15 |
| 2008/0138875 | A1 * | 6/2008 | Atehortua | C12M 21/02 435/171 |
| 2014/0242036 | A1 * | 8/2014 | Castillo | A01N 63/04 424/93.5 |

FOREIGN PATENT DOCUMENTS

| | | |
|---|---|---|
| CN | 1375557 A | 10/2002 |
| CN | 1536069 A | 10/2004 |
| CN | 101492645 A | 7/2009 |
| WO | WO 2008/068602 A2 | 6/2008 |

OTHER PUBLICATIONS

Jiahua Jiang, "Ganoderic acids suppress growth and invasive behavior of breast cancer cells by modulating AP-1 and NF-$_{\kappa}$B signaling", Inernational Journal of Molecular Medicine, vol. 21, pp. 577-584, 2008.
Chyi-Hann Li, et al., "Ganoderic acid X, a lanostanoid triterpene, inhibits topoisomerases and induces apoptosis of cancer cells", Life Sciences, vol. 77, pp. 252-265, 2005.
Chen-Yi Su, et al., "Differential Effectsw of Ganodermic Acid S on the Thromboxane $A_2$-Signaling Pathways in Human Platelets", Biochemical Pharmacology, vol. 58, pp. 587-595, 1999.
Chen-Yi Su, et al., "Predominant inhibition of ganodermic acid S on the thromboxane $A_2$-dependent pathway in human platelets response to collagen", Biochimica et Biophysica Acta, vol. 1437, pp. 223-234, 1999.
Chen-Yi Su, et al., "Potentiation of Ganodermic Acid S on Prostaglandin E1-Induced Cyclic AMP Evaluation in Human Platelets", Thrombosis Research, vol. 99, pp. 135-145, 2000.
Chuen-Neu Wang, et al., "The inhibition of human platelet function by ganodermic acids", Biochem J., vol. 277, pp. 189-197, 1991.
Chuen-Neu Wang, et al., "The aggregation of human platelet induced by ganodermic acid S", Biochimica et Biophysica Acta, vol. 986, pp. 151-160, 1989.
Guan Wang, et al., "Enhancement of IL-2 and IFN-γ expression and NK cells activity involved in the anti-tumor effect of ganoderic acid Me in vivo", International Immunopharmacology, vol. 7, pp. 864-870, 2007.
Qing-Xi, et al., "Protemics Characterization of the Cytotoxicity Mechanism of Ganoderic Acid D and Computer-automated Estimation of the Possible Drug Target Network", Molecular & Cellular Proteomics, Vo. 7.5, pp. 949-961, 2008.

* cited by examiner

*Primary Examiner* — Scott Long
*Assistant Examiner* — Nghi Nguyen
(74) *Attorney, Agent, or Firm* — Muncy, Geissler, Olds & Lowe, P.C.

(57) ABSTRACT

Disclosed herein is an industrial scale process of cultivating cultivating *Ganoderma lucidum* mycelia. As high as 15 Kg dried *Ganoderma lucidum* mycelia may be produced from about 300 liters liquid culture every 30 days, and the resulting dried *Ganoderma lucidum* mycelia are rich in triterpenoids that include at least ganoderic acid S (GAS), ganoderic acid T (GAT), ganoderic acid Me (GAMe), ganoderic acid R (GAR), and ganodermic acid S (GMAS).

9 Claims, 2 Drawing Sheets

INDUSTRIAL SCALE PROCESS OF CULTIVATING *GANODERMA LUCIDUM* MYCELIUM

FIELD OF THE INVENTION

The present disclosure relates to an industrial scale process of cultivating *Ganoderma lucidum*; and particularly, the *Ganoderma lucidum* mycelia, instead of the *Ganoderma lucidum* fruit body.

BACKGROUND OF THE INVENTION

Edible fungus has long been used as a nutritional aid or health food in Asia, with Ling-Zhi, the Chinese name for one form of mushroom *Ganoderma lucidum*, being the most popular and oldest mushroom known to have medicinal usages for thousands years. Various active compounds have been isolated from *Ganoderma* including triterpenoids, polysaccharides, proteins, nucleic acids, polypeptides and phyto-sterols and etc. Among them, triterpenoids are the most important components in Ling-Zhi with significant pharmacological activities such as inhibition of cholesterol synthesis, antitumor, antihypertensive and etc. Triterpenoids are generally known to include various types of ganoderic acids (GAs), ganodermic acids (GMAS), ganoderic alcohols, ganoderic ketones and ganoderic aldehydes and etc. Prior studies have demonstrated that GAs possess cytotoxic and/or anti-proliferative effects against tumor cells. For example, ganoderic acid D (GAD) was found to inhibit the proliferation of HeLa human cervical carcinoma (Yue et al., Mol Cell Proteomics (2008) 7, 949-961); ganoderic acids A and H (GAA and GAH) were demonstrated to suppress growth and invasive behavior of breast cancer cells (Jiang et al., Int J Mol Med (2008) 21, 577-584); ganoderic acid X (GAX) was found to inhibit topoisomerases and induced apoptosis in liver cancer cells (Li et al., Life Sci. (2005) 77, 252-265); and ganoderic acid Me (GAMe) effectively inhibited tumor growth, and lung metastasis (Wang et al., Int Immunopharmacol (2007) 7, 864-870). As to ganodermic acid S (GMAS), it was found to induce aggregation of platelets (Wang et al., Biochim. Biophys. Acta. (1989) 986, 151-160), inhibit function of platelets (Wang et al., Biochem. J. (1991) 277 (Pt 1), 189-197), as well as the signaling cellular responses induced by thromboxane A2 (Su et al., Biochem. Pharmacol. (1999) 58, 587-595; Su et al., Biochim. Biophys. Acta. (1999b) 1437, 223-234) or prostaglandin E1 (Su et al., Thromb. Res. (1999c) 99, 135-145) in platelets.

In the past, Ling-Zhi only grows naturally and rarely on aged trees in steep mountains, however, with the improvement on cultivating techniques, it is now possible to cultivating *Ganoderma lucidum* in artificial environment. JP-A-57014816 disclosed a method of cultivating *Ganoderma lucidum karst*, by planting a seed fungus (spore) into a material wood, however, such method is disadvantages from the viewpoint of productivity, for it takes much labor in inoculation and, the culturing time is long, 120 to 150 days for cultivating, maturing and growing of fungi; and the resulting fungi are different from the naturally grown fungi in terms of the content and/or profiles of the active components (i.e., triterpenoids).

In view of the forgoing, there exists a need in the related art an improved method of cultivating *Ganoderma lucidum* so that large amount of triterpenoids may be produced in a relatively short period of time for medicinal application.

SUMMARY OF THE INVENTION

Accordingly, it is the objective of this disclosure to provide an industrial scale process of cultivating *Ganoderma lucidum*, particularly the mycelium, and not the fruit body, of *Ganoderma lucidum*. As high as 15 Kg dried *Ganoderma lucidum* mycelia may be produced in one batch (i.e., about 300 liters liquid culture) every 30 days, and the resulting dried *Ganoderma lucidum* mycelia are rich in triterpenoids that include at least ganoderic acid S (GAS), ganoderic acid T (GAT), ganoderic acid Me (GAMe), ganoderic acid R (GAR), and ganodermic acid S (GMAS). In a preferred cultivating condition, the *Ganoderma lucidum* mycelia cultivated in according to the method of the present invention contain 28-33 mg triterpenoids/g dried weight.

The industrial scale method of cultivating *Ganoderma lucidum* mycelium includes steps of,
 (a) inoculating the mycelium in no more than 1 liter of a liquid culture medium and culturing for 5 to 15 days;
 (b) inoculating the resulting liquid culture of step (a) in at least 30 liters of the liquid culture medium and culturing for 2 to 5 days;
 (c) inoculating the resulting liquid culture of step (b) in at least 300 liters of the liquid culture medium and culturing for 2 to 5 days; and
 (d) transferring the resulting liquid culture of step (c) into a plurality of culturing plates respectively having a surface area of 1.5-2.5 $cm^2$/mL culture medium, and culturing under an illumination intensity of 200 to 2,000 lux for 10 to 20 days.

According to one preferred embodiment, each of the steps are respectively carried out at a temperature of from 20 to 35° C., a humidity of from 50 to 100%, and an air flow rate of from5 to 200 LPM.

According to one preferred embodiment, steps (a), (b) and (c) are respectively carried out in darkness with a constant stirring at a speed of from 50 to 200 rpm; and the illumination intensity of step (d) is 720 lux.

The liquid culture medium suitable for use in the present method contains at least, glucose, sucrose, peptone, yeast extract, and slat. Optionally, the liquid culture medium may further include soy flour.

According to one preferred embodiment, the method further includes steps of,
 (e) harvesting the mycelia from the culture resulting from the step (d); and
 (f) drying the mycelia of the step (e) until its water content is below 5%, wherein the amount of triterpenoids in the dried mycelia is 28 to 33 mg/g dried weight.

The triterpenoids contained in the dried mycelia obtained by the method of the present invention include, at least, ganoderic acid S (GAS), ganoderic acid T (GAT), ganoderic acid Me (GAMe), ganoderic acid R (GAR), and ganodermic acid S (GMAS).

According to one preferred embodiment of the present disclosure, the number of the plurality of culturing plates in step (d) is 288; and at least 15 Kg of dried *Ganoderma lucidum* mycelia may be obtained every 30 days by the present cultivating method.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF DRAWINGS

The invention can be more fully understood by reading the detailed description of the invention with reference to the accompanying drawings as follows.

DETAILED DESCRIPTION OF THE INVENTION

Figure 1:
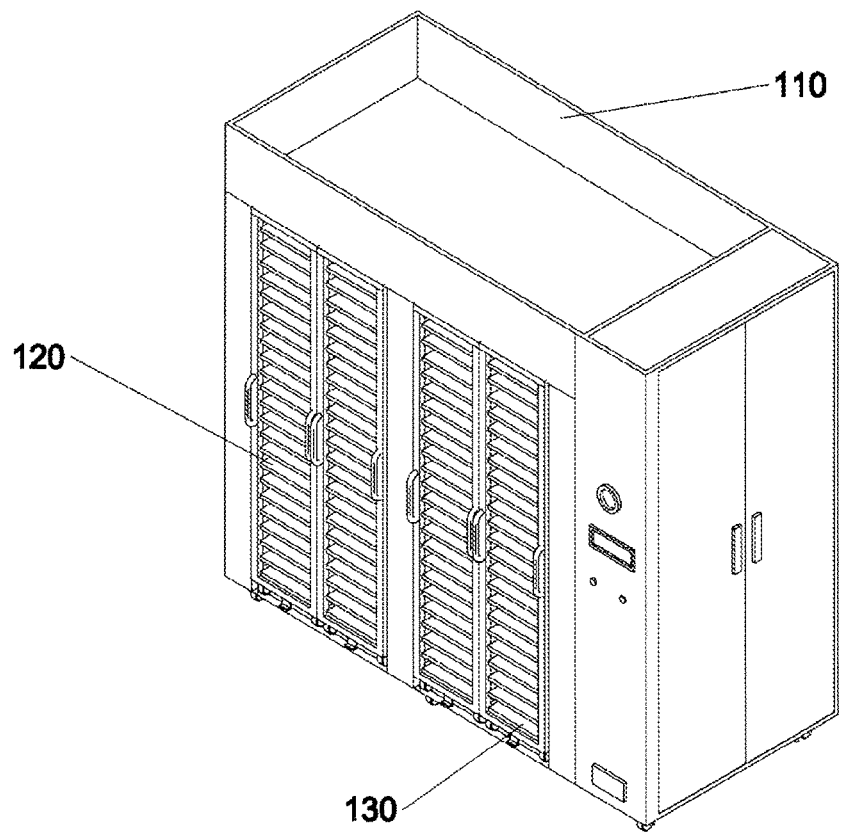
FIG. 1 is a schematic drawing of the cultivating system 100 in according to one embodiment of the present disclosure.

The detailed description provided below in connection with the appended drawings is intended as a description of the present disclosure and is not intended to represent the only forms in which the present disclosure may be constructed or utilized.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The present disclosure is directed to an industrial scale process of cultivating *Ganoderma lucidum* mycelia, in which at least 15 Kg of dried *Ganoderma lucidum* mycelia contains as high as 28-33 mg triterpenoids per 1 g dried weight may be produced in one batch that can be harvested every 30 days. The scale of production may be further expanded simply by multiplying the same operation in duplication, triplication and etc., thereby producing at least 2, 3 or more folds of the dried *Ganoderma lucidum* mycelia thus obtained in one batch of the present method.

The process of the present disclosure includes at least 4 stages of cultivation, in which the culture is expanded at least 10 folds in each stage. In stage I, the process starts by inoculating the *Ganoderma lucidum* mycelium into no more than 1 liter of a first liquid culture medium; and the culture is maintained in a suitable condition for about 5 to 15 days. Preferably, the inoculation is made to no more than 0.8 liter of the first liquid culture medium; and more preferably, no more than 0.5 liter of the first liquid culture medium. The first liquid culture medium contains at least 1.5% glucose, 1.5% sucrose, 0.5% peptone, 0.2% yeast extract, and 0.06% $KH_2PO_4$. After inoculation, the entire culture may be maintained in an environment with constant shaking at a speed from about 50 to 120 rpm, such as 50, 55, 60, 65, 70, 75, 80, 85, 90, 95, 100, 105, 110, 115 or 120 rpm; and at a temperature from about 20 to 35° C., such as 20, 21, 22, 23, 24, 25, 26, 27, 28, 29, 30, 31, 32, 33, 34 or 35° C.; for about 5 to 15 days, such as 5, 6, 7, 8, 9, 10, 11, 12, 13, 14 or 15 days. Preferably, the shaking is carried out at a speed of about 65 to 105 rpm, such as 65, 70, 75, 80, 85, 90, 95, 100, or 105 rpm; at a temperature from about 22 to 33° C., such as 22, 23, 24, 25, 26, 27, 28, 29, 30, 31, 32 or 33° C.; for about 8 to 12 days, such as 8, 9, 10, 11 or 12 days. Most preferably, the shaking is carried out at a speed of about 75 to 90 rpm, such as 75, 80, 85, or 90 rpm, at a temperature from about 25 to 30° C., such as 25, 26, 27, 28, 29, or 30° C.; for about 9 to 11 days. In one preferred example, the stirring is carried out at a speed of 85 rpm at a temperature of 28° C. for 10 days.

In stage II, the resulting liquid culture of stage I is inoculated into at least 30 liters of the fresh first liquid culture medium and continue to culture for 2 to 5 days. Similarly, after inoculation, the entire culture may be maintained in an environment with constant stirring at a speed from about 80 to 200 rpm, such as 80, 85, 90, 95, 100, 105, 110, 115, 120, 125, 130, 135, 140, 145, 150, 155, 160, 165, 170, 175, 180, 185, 190, 195 or 200 rpm; air flow from about 5 to 15 Liters/min (LPM), such as 5, 6, 7, 8, 9, 10, 11, 12, 13, 14, or 15 LPM; and at a temperature from about 20 to 35° C., such as 20, 21, 22, 23, 24, 25, 26, 27, 28, 29, 30, 31, 32, 33, 34 or 35° C.; for about 1 to 5 days, such as 1, 2, 3, 4 or 5 days. Preferably, the stirring is carried out at a speed of about 110 to 170 rpm, such as 110, 115, 120, 125, 130, 135, 140, 145, 150, 155, 160, 165, or 170 rpm; air flow from about 7 to 12 LPM, such as 7, 8, 9, 10, 11, or 12 LPM; at a temperature from about 22 to 33° C., such as 22, 23, 24, 25, 26, 27, 28, 29, 30, 31, 32 or 33° C.; for about 2 to 4 days, such as 2, 3, or 4 days. Most preferably, the stirring is carried out at a speed of about 120 to 160 rpm, such as 120, 125, 130, 135, 140, 145, 150, 155, or 160 rpm; air flow from about 9 to 10 LPM, such as 9 or 10 LPM; at a temperature from about 25 to 30° C., such as 25, 26, 27, 28, 29, or 30° C.; for about 3 days. In one preferred example, the stirring is carried out at a speed of 150 rpm, 10 LPM, at a temperature of 28° C. for 3 days.

In stage III, the resulting liquid culture of stage II is inoculated into at least 300 liters of a second liquid culture medium and continue to culture for 2 to 6 days. The second liquid culture medium contains at least 3% glucose, 6.5% sucrose, 1% peptone, 3% soy flour, 0.6% yeast extract, 0.06% $KH_2PO_4$ and 0.05% $MgSO_4$. After inoculation, the entire culture is maintained in an environment with constant stirring at a speed from about 50 to 150 rpm, such as 50, 55, 60, 65, 70, 75, 80, 85, 90, 95, 100, 105, 110, 115, 120, 125, 130, 135, 140, 145 or 150 rpm; air flow from about 50 to 150 LPM, such as 50, 60, 70, 80, 90, 100, 110, 120, 130, 140, or 150 LPM; and at a temperature from about 20 to 35° C., such as 20, 21, 22, 23, 24, 25, 26, 27, 28, 29, 30, 31, 32, 33, 34 or 35° C.; for about 2 to 6 days, such as 2, 3, 4, 5 or 6 days. Preferably, the stirring is carried out at a speed of about 70 to 130 rpm, such as 70, 75, 80, 85, 90, 95, 100, 105, 110, 115, 120, 125 or 130 rpm; air flow from about 80 to 130 LPM, such as 80, 90, 100, 110, 120 or 130 LPM; at a temperature from about 22 to 33° C., such as 22, 23, 24, 25, 26, 27, 28, 29, 30, 31, 32 or 33° C.; for about 3 to 5 days, such as 3, 4 or 5 days. Most preferably, the stirring is carried out at a speed of about 85 to 115 rpm, such as 85, 90, 95, 100, 105, 110 or 115 rpm, air flow from about 90 to 110 LPM, such as 90, 100, or 110 LPM;, and at a temperature from about 25 to 30° C., such as 25, 26, 27, 28, 29, or 30° C.; for about 4 days. In one preferred example, the stirring is carried out at a speed of 100 rpm, air flow about 100 LPM, at a temperature of 28° C. for 4 days.

In stage IV, the resulting liquid culture of stage III is transferred to a plurality of culturing plates, with each plate having a surface area of 1.5 to 2.5 cm2/mL culture medium, and the culture is maintained under an illumination intensity of about 200 to 2,000 lux for 10 to 20 days. Specifically, about 0.5 to 1 liter of the resulting liquid culture of stage III is poured into each culture plate, which has a surface area of about 1,000 to 2,500 $cm^2$, preferably about 1,500 to 2,000 $cm^2$, more preferably about 1,800 $cm^2$. Up to 288 plates may be used to hold the liquid culture of stage III. The plates may then be stacked up and continue to culture in an environment with controlled temperature, relative humidity, air flow, and illumination. The culture is maintained at a temperature from about 20 to 35° C., such as 20, 21, 22, 23, 24, 25, 26, 27, 28, 29, 30, 31, 32, 33, 34 or 35° C.; relative humidity from about 50 to 100%, such as 50, 60, 70, 80, 90 or 100%; air flow from about 5 to 20 LPM, such as 5, 6, 7, 8, 9, 10, 11, 12, 13, 14, 15, 16, 17, 18, 19, or 20 LPM; illumination intensity from about 100 to 1,000 lux, such as 100, 130, 200, 260, 300, 390, 400, 460, 520, 650, 780, 910 or 1,000 lux; for 10 to 20 days, such as 10, 11, 12, 13, 14, 15, 16, 17, 18, 19 or 20 days. Preferably, the culture is maintained at a temperature from about 22 to 33° C., such as 22, 23, 24, 25, 26, 27, 28, 29, 30, 31, 32, or 33° C.; relative humidity from about 70 to 100%, such as 70, 80, 90 or 100%; air flow from about 8 to 18 LPM, such as 8, 9, 10, 11, 12, 13, 14, 15, 16, 17, or 18 LPM; illumination intensity from about 200 to 780 lux, such as 200, 260, 300, 390, 400, 460, 520, 650, or 780 lux; for 12 to 18 days, such as 12, 13, 14, 15, 16, 17, or 18 days. More preferably, the culture is maintained at a temperature from about 25 to 30° C., such as 25, 26, 27, 28, 29, or 30° C.; relative humidity from about 80 to 100%, such as 80, 90 or 100%; air flow from about 10 to 16 LPM, such as 10, 11, 12, 13, 14, 15, or 16 LPM; illumination intensity from about 300 to 520 lux, such as 300, 390, 400, 460 or 520 lux; for 14 to 16 days, such as 14, 15, or 16 days. In one preferred example, the culture is maintained in the environment with the air flow of about 15 LPM, temperature about 28° C., 100% relative humidity, illumination intensity about 460 lux for 14 days.

Figure 2:
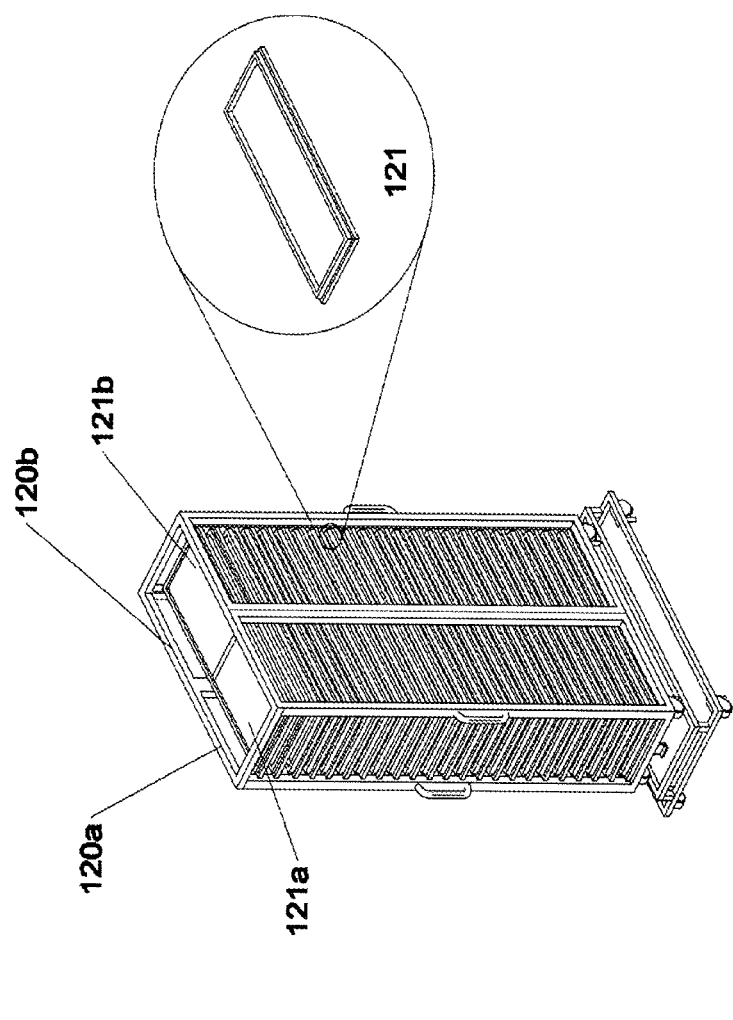
FIG. 2 is another schematic drawing illustrating the cultivating plate 121a and the cultivating rack 120 in according to one embodiment of the present disclosure.
Figure 2:
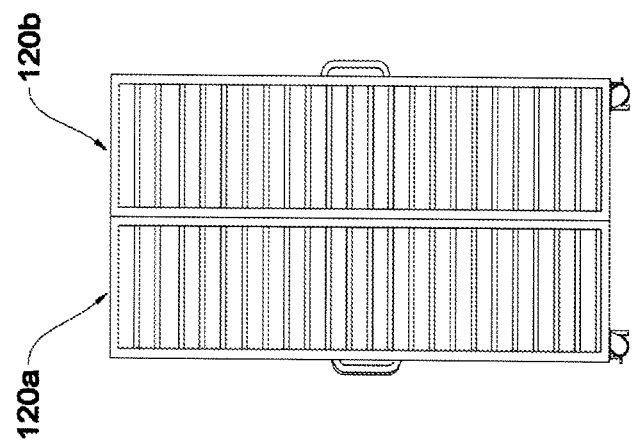

Typically, the culture in stage IV is maintained in a cultivating system as illustrated in FIG. 1. The cultivating system 100 of this invention includes a housing 110, and at least four cultivating racks, and only two cultivating racks (120, 130) are depicted in FIG. 1. Each rack 120 consists of two columns (120a, 120b), with each column capable of holding at least one cultivating plate (121a). The cultivating plate may be made of steel or plastic; and may be in any suitable shape or size. In the preferred example as depicted in FIG. 2, the cultivating plate is made of steel, and is about 40 cm in width, 60 cm in length and about 5 cm in height. At most 36 plates can be stacked and held in each columns (120a, 120b), which leads to a maximum of 72 plates in one rack, and a total of 288 plates that may be housed in the cultivating system 100 of this invention.

The *Ganoderma lucidum* mycelia thus harvested by the cultivating process described above is then air dried at a temperature below 70° C., preferably below 60° C., until the water content of the dried *Ganoderma lucidum* mycelia is below 10%, preferably below 5%, and most preferably below 3%.

In general, about 10 to 20 Kg, preferably about 13 to 17 Kg, and more preferably about 15 Kg dried *Ganoderma lucidum* mycelia may be obtained from one batch of the process or from expanding about 300 liters of the liquid culture of stage III of the present process.

The thus obtained dried *Ganoderma lucidum* mycelia includes about 28-33 mg triterpenoid per one gram of dried *Ganoderma lucidum* mycelia, preferably about 30 mg triterpenoid per one gram of dried *Ganoderma lucidum* mycelia. The triterpenoid comprises at least ganoderic acid S (GAS), ganoderic acid T (GAT), ganoderic acid Me (GAMe), ganoderic acid R (GAR), and ganodermic acid S (GMAS).

Further, any person skilled in the related art may be easily scaled up the production of triterpenoids by multiplying (e.g., duplicating, triplicating, and etc) the cultivating process described herein in case a large production of triterpenoids is required.

The present invention will now be described more specifically with reference to the following embodiments, which are provided for the purpose of demonstration rather than limitation.

EXAMPLES

Example 1

Cultivating *Ganoderma lucidum* Mycelia in Industrial Scale 1.1 Production of Liquid Culture I About 1 $cm^2$ of *Ganoderma lucidum* mycelia was inoculated into 400 mL liquid culture medium 1, which contains 1.5% glucose, 1.5% sucrose, 0.5% peptone, 0.2% yeast extract, and 0.06% $KH_2PO_4$. The entire culture was then maintained in an environment with constant stirring at 85 rpm at a temperature of about 28° C. for 10 days, and the resulted culture was termed "liquid culture I."

1.2 Production of Liquid Culture II

In a fermentation tank about 50 liters in volume, 30 liters of the liquid culture medium 1 was added, then 2.8 liters of the liquid culture I of example 1.1 was inoculated. The entire culture was then maintained in an environment with constant stirring at 150 rpm, air flow at 10 LPM, at a temperature of about 28° C. for 3 days, and the resulted culture was termed "liquid culture II."

1.3 Production of Liquid Culture III

In a fermentation tank about 500 liters in volume, 300 liters of the liquid culture medium 2 was added, which contains 3% glucose, 6.5% sucrose, 3% soy flour, 1% peptone, 0.6% yeast extract, 0.06% $KH_2PO_4$, and 0.05% $MgSO_4$. Then, 50 liters of the liquid culture II of example 1.2 was inoculated. The entire culture was then maintained in an environment with constant stirring at 100 rpm, air flow at 100 LPM, temperature of about 28° C. for 4 days, and the resulted culture was termed "liquid culture III."

1.4 Expanding the Culture of Liquid Culture III

In 288 metal culture plates (each plate is 30 cm×50 cm×5 cm), about 1 liter of the liquid culture III of example 1.3 was added to each plate under sterilized condition, and then the plates were respectively loaded into the cultivating racks (120, 130) and placed into the cultivating system 110 as depicted in FIG. 1, in which the culture was maintained in an environment with the relative humidity of 100%, air flow at 15 LPM, temperature of 28° C., and the illumination intensity of 460 lux for 14 days. The mycelia were then collected and dried at 60° C. until the water content was below 5%.

Example 2

Effects of Cultivating Factors on the Level of Triterpenoids in The *Ganoderma lucidum* Mycelia of Example 1

In this example, cultivating factors were varied so as to find out the optimal conditions for cultivating the liquid culture III or *Ganoderma lucidum* mycelia of example 1.3. The cultivating factors that were investigated included the followings: illumination intensity from 0 to 720 lux; air flow from 0 to 30 LPM; the relative humidity (RH) from 50 to 100%; and the temperature from 23 to 33° C. The mycelia were then respectively collected and dried at 60° C. until the water content of each harvest was below 5%, and the total amount of triterpenoids, which includes GAT, GAS, GAR, GAMe and GMAS, was measured. Results are summarized in Tables 1 to 5.

TABLE 1

Effect of Illumination Intensity On the Level of Triterpenoids In The Cultivated *Ganoderma lucidum* Mycelia of Example 1

| Illumination Intensity (Lux) | Dried Mycelia (g/L) | Triterpenoids (mg/g dried mycelia) |
|---|---|---|
| 0 | 24.23 | 9.11 |
| 260 | 33.27 | 26.66 |
| 520 | 34.51 | 28.11 |
| 780 | 33.64 | 27.84 |

Note:
the culture was maintained at 28° C., 5 LPM, and 80% RH.

TABLE 2

Effect of Flow of Air On the Level of Triterpenoids In The Cultivated *Ganoderma lucidum* Mycelia of Example 1

| Flow of Air (Liters/min, LPM) | Dried Mycelia (g/L) | Triterpenoids (mg/g dried mycelia) |
|---|---|---|
| 0 | 21.01 | 8.29 |
| 5 | 29.21 | 13.08 |
| 15 | 32.20 | 28.14 |
| 30 | 34.82 | 25.33 |

Note:
the culture was maintained at 28° C., 260 lux, and 80% RH.

TABLE 3

Effect of Relative Humidity On the Level of Triterpenoids In The Cultivated *Ganoderma lucidum* Mycelia of Example 1

| Relative Humidity (%, RH) | Dried Mycelia (g/L) | Triterpenoids (mg/g dried mycelia) |
|---|---|---|
| 50 | 36.11 | 7.22 |
| 80 | 34.33 | 29.19 |
| 95 | 32.22 | 32.11 |

Note:
the culture was maintained at 28° C., 260 lux, and 5 LPM.

TABLE 4

Effect of Temperature On the Level of Triterpenoids In The Cultivated *Ganoderma lucidum* Mycelia of Example 1

| Temperature (° C.) | Dried Mycelia (g/L) | Triterpenoids (mg/g dried mycelia) |
|---|---|---|
| 23 | 31.02 | 26.31 |
| 28 | 34.68 | 33.15 |
| 33 | 36.72 | 25.67 |

Note:
the culture was maintained at 260 lux, 5 LPM, and 80% RH.

TABLE 5

Effect of The Number of Cultivating Plates Per Rack On the Level of Triterpenoids In The Cultivated *Ganoderma lucidum* Mycelia of Example 1

| No. of Plates/ Column | Dried Mycelia (g/L) | Triterpenoids (mg/g dried mycelia) |
|---|---|---|
| 18 | 29.10 | 27.56 |
| 36 | 34.12 | 30.86 |
| 72 | 36.24 | 31.28 |

Note:
the culture was maintained at 260 lux, 5 LPM, and 80% RH.

Taken together the results from Tables 1 to 5, it appears that the level of triterpenoids in the cultivated *Ganoderma L.* mycelia increased significantly if they were illuminated in the last stage of cultivation, an intensity of 260 lux was sufficient enough to increase the total level of triterpenoids for about 3 folds from 9.11 mg/g to 26.66 mg/g (see Table 1). As to the rest cultivating parameters that had significant impacts on the total triterpenoids, air flow, RH and temperature were preferably set at 15 LPM, 80%, and 28° C., respectively (see Tables 2, 3 and 4).

Since the cultivation was taken place in the cultivation system as depicted in FIG. 1, which contains two cultivating racks, with each rack capable of holding at most 72 cultivating plates (or 36 plates per column), it appears that total level of triterpenoids in the cultivated *Ganoderma L.* mycelia was somewhat diminished if the number of plates was not high enough (see Table 5, 18 plates/column vs 72 plates/column), and the diminish in total level of triterpenoids might be resulted from the lowering in RH in the culture system (i.e., unable to maintain 80% RH) caused by insufficient culture of *Ganoderma L.*

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. An industrial scale method of cultivating *Ganoderma lucidum* mycelium comprising,
    (a) inoculating the mycelium in no more than 1 liter of a liquid culture medium and culturing for 5 to 15 days;
    (b) inoculating the resulting liquid culture of step (a) in at least 30 liters of the liquid culture medium and culturing for 2 to 5 days;

(c) inoculating the resulting liquid culture of step (b) in at least 300 liters of the liquid culture medium and culturing for 2to 5 days; and (d) transferring the resulting liquid culture of step (c) into a plurality of culturing plates respectively having a surface area of 1.5 to 2.5 cm$^2$/mL culture medium, and culturing under an illumination intensity of 200 to 2,000 lux for 10 to 20 days;

wherein steps (a), (b) and (c) are respectively carried out in darkness, and each steps are respectively carried out at a temperature from 20 to 35° C., a humidity from 50 to 100%, and an air flow from 5 to 200 LPM.

2. The method of claim 1, wherein the culture plate has a surface area of 1.8 cm$^2$/mL culture medium.

3. The method of claim 1, wherein the liquid culture media comprises glucose, sucrose, peptone, yeast extract, and slat.

4. The method of claim 3, wherein the liquid culture media further comprises soy flour.

5. The method of claim 2, wherein the illumination intensity of step (d) is 460 lux.

6. The method of claim 2, wherein the number of the plurality of culturing plates is 288.

7. The method of claim 2, further comprising, (e) harvesting the mycelia from the culture resulting from step (d); and (f) drying the mycelia of step (e) until its water content is below 5%, wherein the amount of triterpenoids in the dried mycelia is 28 to 33 mWg dried weight.

8. The method of claim 7, wherein the triterpenoids comprises ganoderic acid S (GAS), ganoderic acid T (GAT), ganoderic acid Me (GAMe), ganoderic acid R (GAR), and ganodermic acid S (GMAS).

9. The method of claim 7, wherein about 15 Kg of dried *Ganoderma lucidum* mycelia is produced.

* * * * *